(12) United States Patent
Sugahara

(10) Patent No.: US 9,088,893 B2
(45) Date of Patent: Jul. 21, 2015

(54) CONTROL SYSTEM, CONTROLLED APPARATUS, AND OPERATION CONTROL METHOD

(71) Applicant: FUJIFILM Corporation, Tokyo (JP)

(72) Inventor: Mayuko Sugahara, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 111 days.

(21) Appl. No.: 13/844,907

(22) Filed: Mar. 16, 2013

(65) Prior Publication Data

US 2013/0263229 A1 Oct. 3, 2013

(30) Foreign Application Priority Data

Mar. 29, 2012 (JP) ................................. 2012-075837

(51) Int. Cl.
| | |
|---|---|
| *G06F 7/04* | (2006.01) |
| *H04W 12/06* | (2009.01) |
| *H04L 9/32* | (2006.01) |
| *A61B 6/00* | (2006.01) |
| *H04L 29/06* | (2006.01) |

(52) U.S. Cl.
CPC ............... *H04W 12/06* (2013.01); *A61B 6/548* (2013.01); *H04L 9/3226* (2013.01); *H04L 63/083* (2013.01)

(58) Field of Classification Search
None
See application file for complete search history.

(56) References Cited

U.S. PATENT DOCUMENTS

| | | | | |
|---|---|---|---|---|
| 2002/0138632 | A1* | 9/2002 | Bade et al. ................... | 709/229 |
| 2004/0187018 | A1* | 9/2004 | Owen et al. .................. | 713/200 |
| 2006/0255904 | A1* | 11/2006 | Danzer et al. ................ | 340/5.2 |
| 2007/0192841 | A1* | 8/2007 | Kim ............................... | 726/5 |
| 2009/0132544 | A1* | 5/2009 | Hattori ........................... | 707/10 |
| 2009/0199278 | A1* | 8/2009 | Song ............................... | 726/6 |
| 2010/0107229 | A1* | 4/2010 | Najafi et al. ..................... | 726/6 |

(Continued)

FOREIGN PATENT DOCUMENTS

| | | |
|---|---|---|
| JP | 2004-240806 A | 8/2004 |
| JP | 2007-208887 A | 8/2007 |
| JP | 2007208887 A * | 8/2007 |

OTHER PUBLICATIONS (Snapshot of NPL).*

(Continued)

*Primary Examiner* — Eleni Shiferaw
*Assistant Examiner* — Demaris Brown
(74) *Attorney, Agent, or Firm* — McGinn IP Law Group, PLLC.

(57) ABSTRACT

A control system includes a controlled apparatus and a portable terminal apparatus that controls the controlled apparatus. The controlled apparatus includes an authentication code generating unit that generates an authentication code and an authentication code output unit that outputs the generated authentication code. The portable terminal apparatus includes a code input unit that inputs a code and a code transmitting unit that transmits the input code to the controlled apparatus. The controlled apparatus further includes a determining unit that determines whether the code transmitted from the code transmitting unit is the authentication code output from the authentication code output unit and whether a first period has elapsed since generation of the authentication code and a permission unit that permits control using the portable terminal apparatus in response to determination that the transmitted code is the output authentication code and the first period has not elapsed.

17 Claims, 16 Drawing Sheets

(56) References Cited

U.S. PATENT DOCUMENTS

2010/0122330 A1* 5/2010 McMillan et al. ............... 726/6
2012/0016985 A1* 1/2012 Tullberg et al. ............. 709/224
2012/0124656 A1* 5/2012 Senac ............................. 726/9
2012/0314859 A1* 12/2012 Ksontini et al. ............. 380/247

OTHER PUBLICATIONS

Hou et al., "Chorus: Scalable In-band Trust Establishment for Multiple Contrained Devices Over the Insecure Wireless Channel," Apr. 2013, ACM, p. 167-178.*

Law et al., "Comparative Study of Multicast Authentication Schemes with Application to Wide-Area Measurement System," May 2013, ACM, p. 287-298.*

Mondal et al., "Secure and Simplified Access to Home Appliances Using Iris Recognition," 2009, IEEE, p. 22-29.*

Roy et al., "Iris Recognition: A Java Based Implementation," 2007, IEEE, p. 1-6.*

Notice of Reasons for Rejection dated Apr. 8, 2014 (with Partial English language Translation).

* cited by examiner

FIG. 5

AUTHENTICATION CODE TABLE

| AUTHENTICATION CODE | GENERATION DATE AND TIME |
|---|---|
| ABCDE | 02-19-2012 10:30 |
| FGHIJ | 02-20-2012 13:10 |
| ⋮ | ⋮ |
| LMNOP | 03-15-2012 14:40 |

FIG. 7

AUTHENTICATED TERMINAL ID TABLE

| AUTHENTICATED TERMINAL ID | ACCESS PERMISSION DATE AND TIME |
|---|---|
| ID1 | 03-15-2012 10:30 |
| ID2 | 03-15-2012 15:15 |

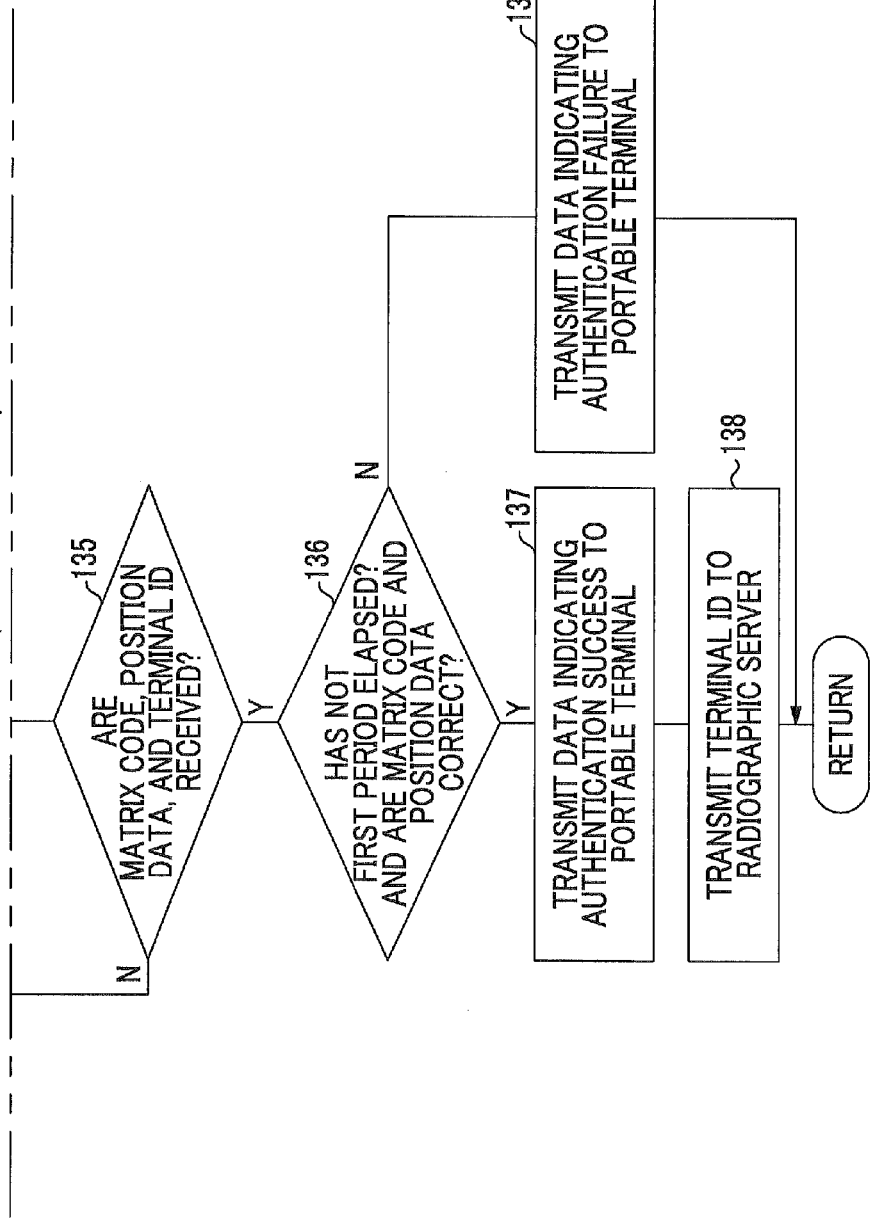

CONTROL SYSTEM, CONTROLLED APPARATUS, AND OPERATION CONTROL METHOD

BACKGROUND OF THE INVENTION

1. Field of the Invention

The present invention relates to a control system, a controlled apparatus, and an operation control method.

2. Description of the Related Art

In an aspect of a radiographic system, an installation-type terminal apparatus is arranged in an operating room and a radiographic apparatus is arranged in a radiographic room. The radiographer positions the patient in the radiographic room and performs a radiographing operation in the operating room. Since the installation-type terminal apparatus is arranged in the operating room, it is difficult to position the patient in the radiographic room while viewing a display screen provided in the installation-type terminal apparatus. In another aspect of the radiographic system, a portable terminal apparatus can be used in addition to the structure in which the installation-type terminal apparatus is arranged in the operating room and the radiographic apparatus is arranged in the radiographic room. The same operation as that of the installation-type terminal apparatus can be performed by the portable terminal apparatus. Therefore, it is possible to position the patient in the radiographic room while viewing the display screen provided in the portable terminal apparatus.

JP2006-314791A discloses a medical examination or medical treatment apparatus in which the remote operation of an X-ray apparatus 2 is available when an operation element 8 is disposed in a room 12 and the remote operation of the X-ray apparatus 2 is unavailable when the operation element 8 is disposed outside the room 12. JP2009-77968A discloses a method in which a code 3 is allocated to a rack on which a medical apparatus 7 is mounted and a reading device 9 reads the code 3 for reserving the medical apparatus 7. In addition, JP2011-100287A discloses a method which permits the execution of a program 101 only under illumination light 200.

When the portable terminal apparatus is used to operate the radiographic apparatus, the portable terminal apparatus is carried out of the X-ray room or the operating room. In order to ensure security, it is necessary to prevent the portable terminal apparatus from being operated at a location outside the X-ray room or the operating room. IDs or passwords may be used to strengthen security. However, in this case, there is a concern that the IDs or the passwords will leak. In addition, in the case where an ID card is used for authentication, installation costs may be required. Furthermore, in the case of biometric authentication, it is difficult to perform authentication when a person wears a mask or gloves, or when a person becomes old, or when a person is wounded or injured.

In JP2006-314791A, JP2009-77968A, and JP2011-100287A, the enusuring of security is not taken in consideration in using the portable terminal apparatus to operate a controlled apparatus such as a radiographic apparatus.

SUMMARY OF THE INVENTION

Therefore, an object of the present invention is to provide a control system, a controlled apparatus, and an operation control method capable of ensuring security when a portable terminal apparatus is used to operate the controlled apparatus.

According to an aspect of the present invention, there is provided a control system including a controlled apparatus and a portable terminal apparatus that controls the controlled apparatus.

The controlled apparatus includes an authentication code generating unit that generates an authentication code and an authentication code output unit that outputs the authentication code generated by the authentication code generating unit. The portable terminal apparatus includes a code input unit that inputs a code and a code transmitting unit that transmits the code input from the code input unit to the controlled apparatus.

The controlled apparatus further includes a determining unit that determines whether the code transmitted from the code transmitting unit of the portable terminal apparatus is the authentication code output from the authentication code output unit of the controlled apparatus and whether a first period has elapsed since generation of the authentication code by the authentication code generating unit of the controlled apparatus and a permission unit that permits control using the portable terminal apparatus in response to determination by the determining unit that the code transmitted from the code transmitting unit of the portable terminal apparatus is the authentication code output from the authentication code output unit of the controlled apparatus and the first period has not elapsed.

According to another aspect of the present invention, there is provided an operation control method suitable for a control system. That is, there is provided a method of controlling an operation of a control system including a controlled apparatus and a portable terminal apparatus that controls the controlled apparatus. The method includes: allowing an authentication code generating unit of the controlled apparatus to generate an authentication code; allowing an authentication code output unit of the controlled apparatus to output the authentication code generated by the authentication code generating unit; allowing a code input unit of the portable terminal apparatus to input a code; allowing a code transmitting unit of the portable terminal apparatus to transmit the code input from the code input unit to the controlled apparatus; allowing a determining unit of the controlled apparatus to determine whether the code transmitted from the code transmitting unit of the portable terminal apparatus is the authentication code output from the authentication code output unit of the controlled apparatus and whether a first period has elapsed since generation of the authentication code by the authentication code generating unit of the controlled apparatus; and allowing a permission unit of the controlled apparatus to permit control using the portable terminal apparatus in response to determination by the determining unit that the code transmitted from the code transmitting unit of the portable terminal apparatus is the authentication code output from the authentication code output unit of the controlled apparatus and the first period has not elapsed.

The controlled apparatus and the portable terminal apparatus may be independently provided.

According to the above-mentioned aspect, the controlled apparatus generates the authentication code and outputs the generated authentication code. The user with the portable terminal apparatus moves near the controlled apparatus to get the authentication code output from the authentication code output unit of the controlled apparatus. When the output authentication code is input to the portable terminal apparatus, the input authentication code is transmitted to the controlled apparatus. Then, the determination is made as to whether the input authentication code is the authentication code output from the authentication code output unit of the controlled apparatus and whether the first period has elapsed since the generation of the authentication code. When the determination is made that the input authentication code is the authentication code output from the authentication code output unit of the controlled apparatus and that the first period has not elapsed since the generation of the authentication code, the portable terminal apparatus is permitted to control the controlled apparatus.

If the authentication code input to the portable terminal apparatus is identical to the authentication code output from the authentication code output unit of the controlled apparatus, it means that the user with the portable terminal apparatus is close to the controlled apparatus. Since it is considered that only the user who is authorized to control the controlled apparatus can approach the controlled apparatus, the user can use the portable terminal apparatus to control the controlled apparatus. The control of the controlled apparatus by the portable terminal apparatus with the authentication code is not permitted in the case the first period has passed since the generation of the authentication code. Therefore, it is possible to prevent the controlled apparatus from being controlled again by a user just because the user has approached the controlled apparatus once.

The controlled apparatus may further include a cancellation unit that cancels permission of the control using the portable terminal apparatus in response to elapse of a second period (which may be equal to the first period) since the permission by the permission unit.

The portable terminal apparatus may further include a position data transmitting unit that transmits data indicating a position of the portable terminal apparatus to the controlled apparatus in response to input of the code from the code input unit. In this case, for example, the determining unit of the controlled apparatus may determine whether the code transmitted from the code transmitting unit of the portable terminal apparatus is the authentication code output from the authentication code output unit of the controlled apparatus, whether the first period has elapsed, and whether the position data transmitted from the position data transmitting unit of the portable terminal apparatus indicates a position of the controlled apparatus. The permission unit of the controlled apparatus may permit the control using the portable terminal apparatus in response to determination by the determining unit that the code transmitted from the code transmitting unit of the portable terminal apparatus is the authentication code output from the authentication code output unit of the controlled apparatus, the first period has not elapsed, and the position data transmitted from the position data transmitting unit of the portable terminal apparatus indicates the position of the controlled apparatus.

The controlled apparatus may include, for example, a controlled apparatus body, an authentication server, and a control server which are configured to communicate with one another. In this case, the authentication server may include, for example, the authentication code generating unit and an authentication code transmitting unit that transmits the authentication code generated by the authentication code generating unit to the controlled apparatus body. The controlled apparatus body may include, for example, the authentication code output unit. The authentication code output unit may output the authentication code transmitted from the authentication code transmitting unit of the authentication server. The authentication server may include, for example, the determining unit and a determination result transmitting unit that transmits data indicating a result of the determination by the determining unit to the control server. The control server may include, for example, the permission unit. The permission unit may permits the control based upon the data indicating the result of the determination result which is transmitted from the determination result transmitting unit of the authentication server.

The controlled apparatus may be arranged in, for example, an authentication area and the portable terminal apparatus may control the controlled apparatus both inside and outside the authentication area.

According to the present invention, it is possible to provide a control system, a controlled apparatus, and an operation control method capable of ensuring security when a portable terminal apparatus is used to operate the controlled apparatus.

BRIEF DESCRIPTION OF THE DRAWINGS

FIG. 5 shows an example of an authentication code table.
FIG. 7 shows an example of an authenticated terminal ID table.

DESCRIPTION OF THE PREFERRED EMBODIMENTS

Figure 1:
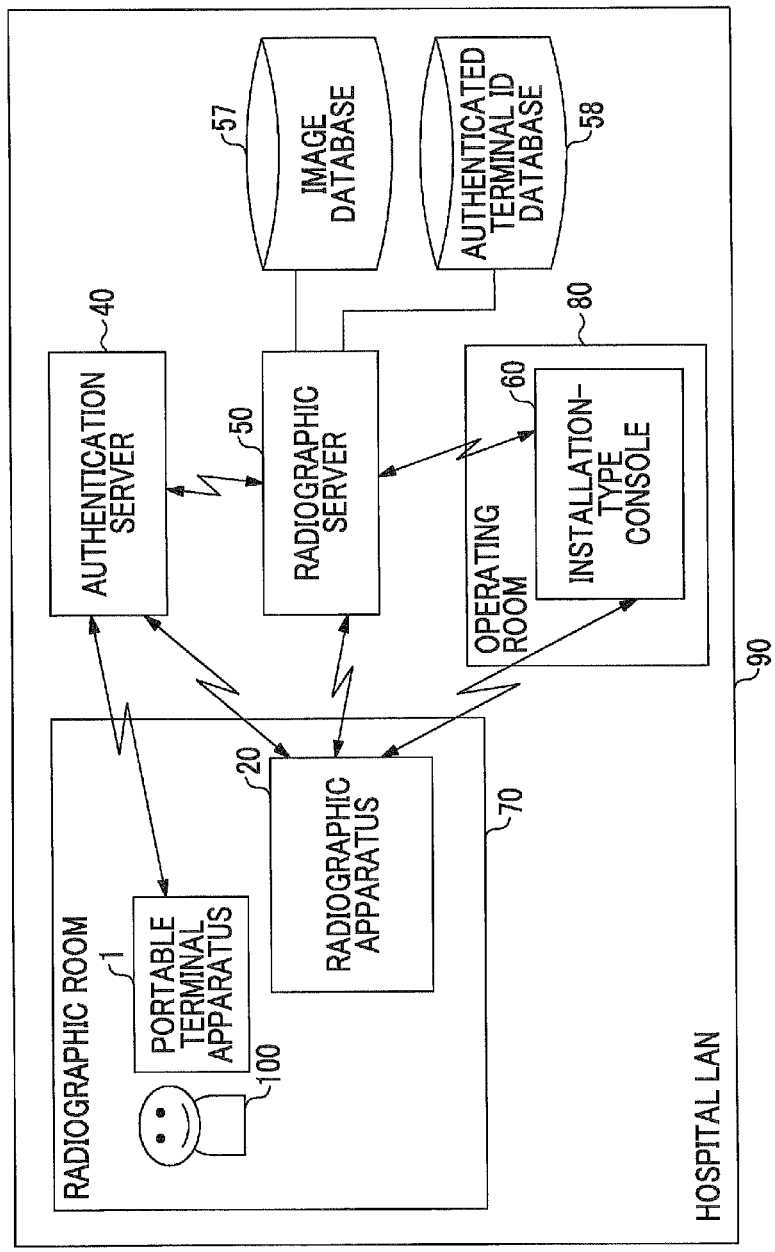
FIG. 1 shows an aspect of the inside of a hospital.

FIG. 1 is a diagram illustrating a control system according to an embodiment and shows an example of the control system in a hospital.

A radiographic room 70 (authentication area) is provided in the hospital. A radiographic apparatus 20 (controlled apparatus body) which captures a radiological image of a subject is arranged in the radiographic room 70. An installation-type console 60 which controls the radiographic apparatus 20 is installed in an operating room 80 different from the radiographic room 70. In addition, an authentication server 40 and a radiographic server 50 (control server) are installed in the hospital. That is, in this embodiment, for example, the radiographic apparatus 20, the authentication server 40, and the radiographic server 50 form a controlled apparatus. The authentication server 40 and/or the radiographic server 50 may not be necessarily installed in the hospital as long as they can communicate with, for example, the radiographic apparatus 20, as described later. The radiographic server 50 is connected to an image database 57 and an authenticated terminal ID database 58.

The radiographic apparatus 20 is controlled by both the installation-type console 60 installed in the operating room 80 and a portable terminal apparatus 1 which can be freely carried by an operator 100.

A hospital LAN (Local Area Network) 90 is installed in the hospital. The hospital LAN 90 enables the authentication server 40 to wirelessly communicate with the portable terminal apparatus 1, the radiographic apparatus 20 and the radiographic server 50. In addition, the installation-type console 60 can wirelessly communicate with the radiographic apparatus 20 and the radiographic server 50.

Since the portable terminal apparatus 1 can be freely carried by the operator, the operator 100 with the portable terminal apparatus 1 can enter the radiographic room 70 and position the subject while viewing a display screen of the portable terminal apparatus 1.

Figure 2:
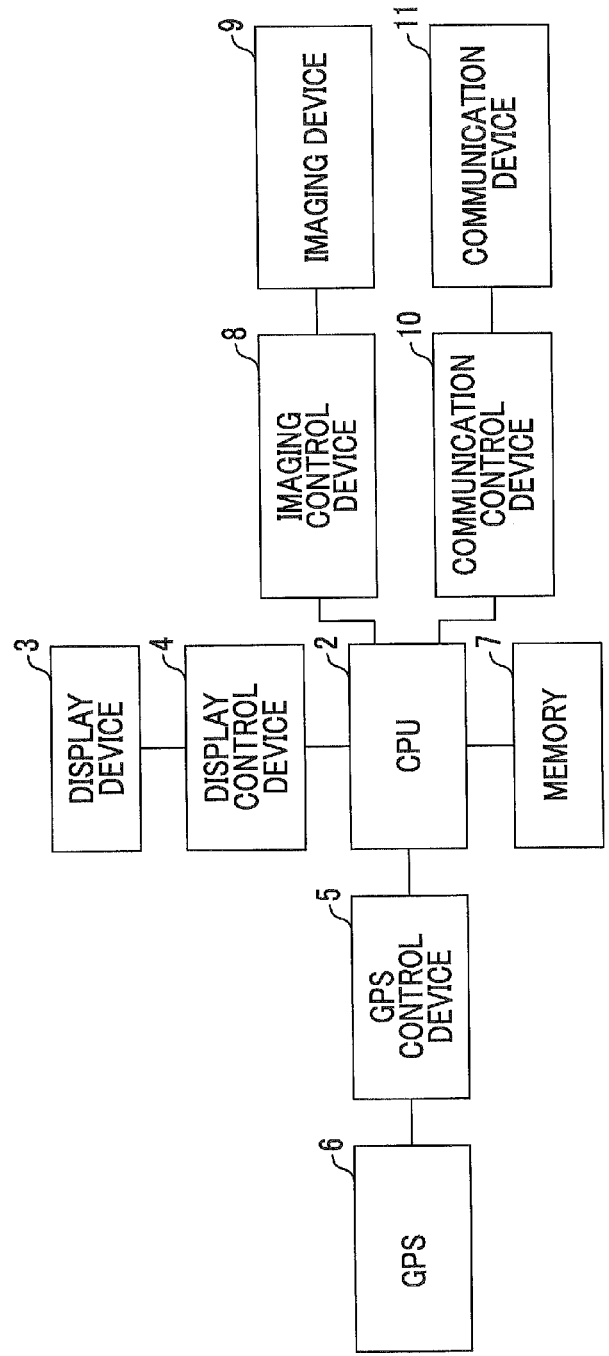
FIG. 2 is a block diagram illustrating the electrical configuration of a portable terminal apparatus.

FIG. 2 is a block diagram illustrating the electrical configuration of the portable terminal apparatus 1.

The overall operation of the portable terminal apparatus 1 is controlled by a CPU 2.

The portable terminal apparatus 1 includes a display device 3, a display control device 4 that controls the display device 3, a GPS (Global Positioning System) device 6 that detects the position of the portable terminal apparatus 1, a GPS control device 5 that controls the GPS device 6, and a memory 7 that stores, for example, predetermined data and programs. In addition, the portable terminal apparatus 1 includes an imaging device 9, an imaging control device 8 that controls the imaging device 9, a communication device 11, and a communication control device 10 that controls the communication device 11. A touch panel (not shown) is formed on the display screen of the display device 3. The touch panel is used to input, for example, a desired command to the portable terminal apparatus 1.

Figure 3:
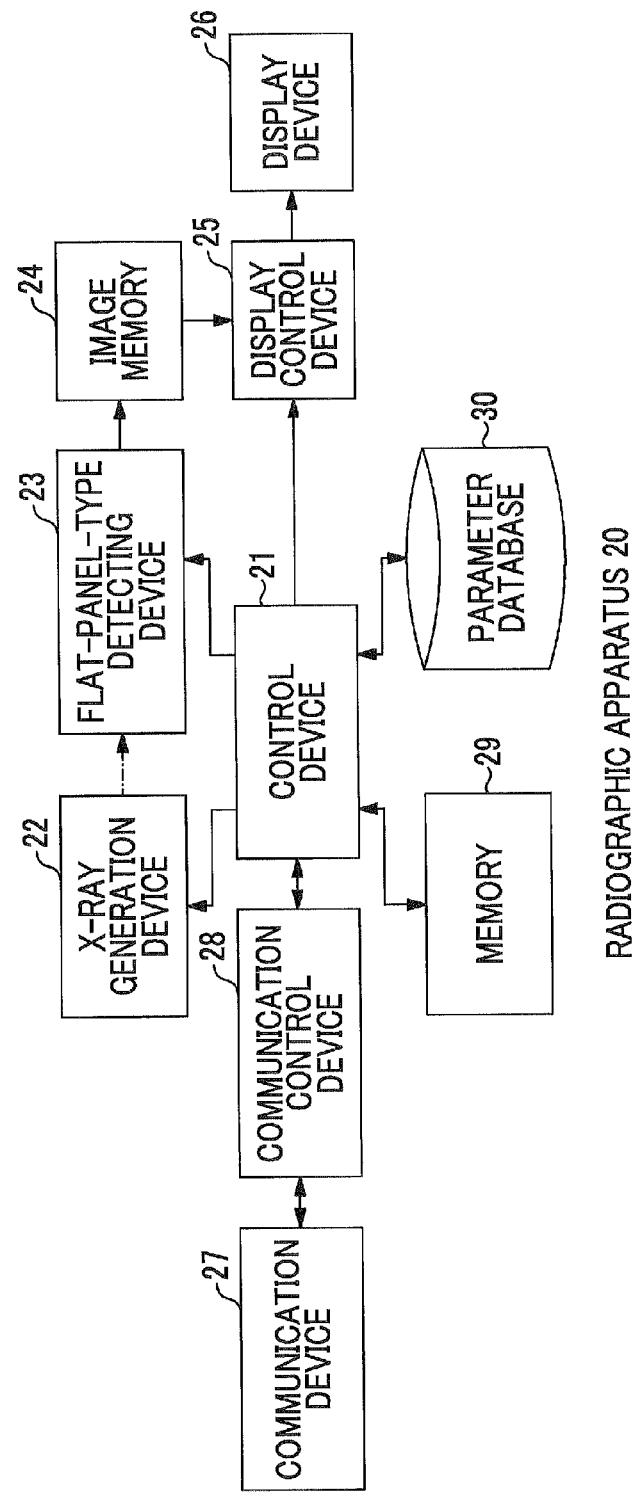
FIG. 3 is a block diagram illustrating the electrical configuration of a radiographic apparatus.

FIG. 3 is a block diagram illustrating the electrical configuration of the radiographic apparatus 20.

The overall operation of the radiographic apparatus 20 is controlled by a control device 21.

The radiographic apparatus 20 includes an X-ray generating device 22 and a flat-panel-type detecting device 23. The subject goes between the X-ray generating device 20 and the flat panel-type detecting device 23, X-rays radiated from the X-ray generating device 22 pass through the subject, and the flat panel-type detecting device 23 detects the X-rays. In this way, the radiological image of the subject is obtained. The obtained radiological image is temporarily stored in the image memory 24. The radiological image stored in the image memory 24 is displayed on the display screen of the display device 26 by the display control device 25.

As described above, the radiographic apparatus 20 further includes a communication device 27 that communicates with, for example, the authentication server 40, a communication control device 28 that controls the communication device 27, a memory 29 that stores, for example, predetermined data and programs, and a parameter database 30 that stores radiographic parameters. Image data indicating the radiological image which is obtained by radiography may be transmitted to the radiographic server 50 by the communication device 27.

A matrix code (two-dimensional code) indicating an authentication code is displayed on the display screen of the display device 26. The portable terminal apparatus 1 is used to capture the matrix code to authenticate the portable terminal apparatus 1, which will be described. The authenticated portable terminal apparatus 1 can be used to control the radiographic apparatus 20.

Figure 4:
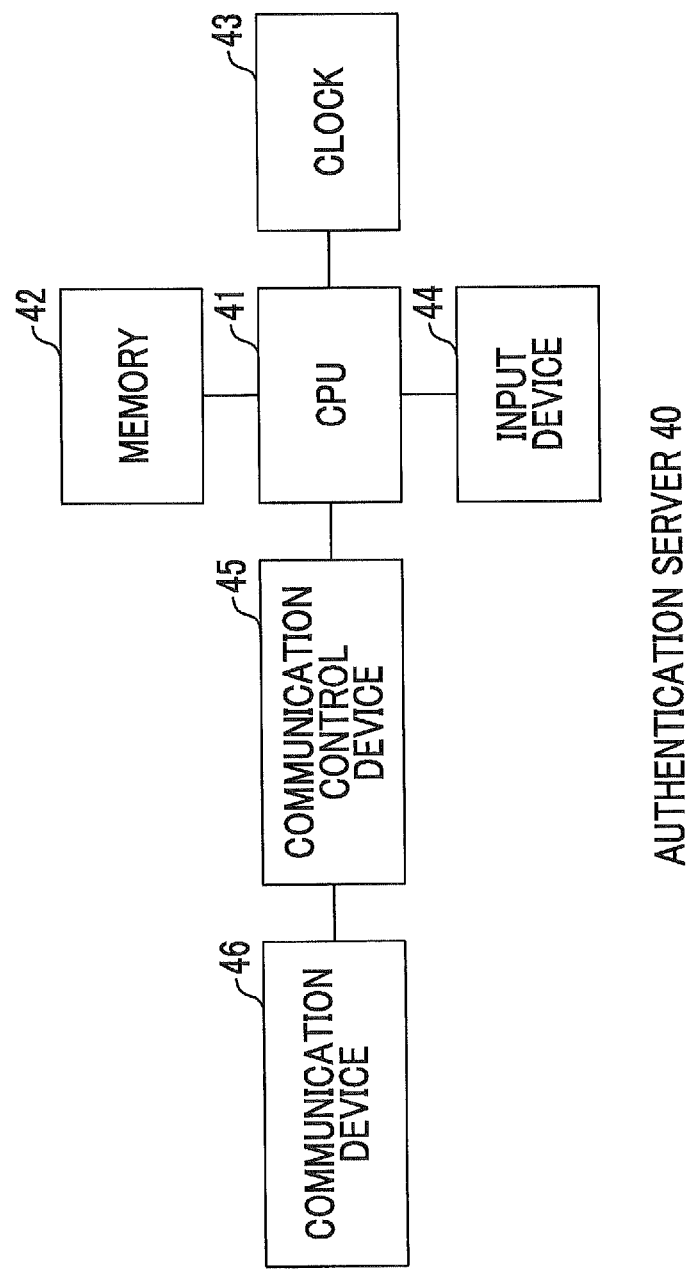
FIG. 4 is a block diagram illustrating the electrical configuration of an authentication server.

FIG. 4 is a block diagram illustrating the electrical configuration of the authentication server 40.

The overall operation of the authentication server 40 is controlled by a CPU 41.

The authentication server 40 includes a memory 42 that stores predetermined data and programs, a clock 43, and an input device 44 such as a keyboard. In addition, the authentication server 40 includes a communication device 46 that communicates with, for example, the radiographic apparatus 20 and a communication control device 45 that controls the communication device 46, as described above.

FIG. 5 shows an example of an authentication code table.

As described above, the authentication code table is used to authenticate the portable terminal apparatus 1. When the radiographic apparatus 20 transmits an authentication code request command to the authentication server 40, the CPU 41 which serves as an authentication code generating unit in the authentication server 40 generates a valid authentication code during the first period. The date and time when the authentication code is generated are also stored in the authentication code table. In the case where the first period has elapsed from the date and time when the authentication code has been generated, the authentication code is invalid even though it is stored in the authentication code table.

Figure 6:
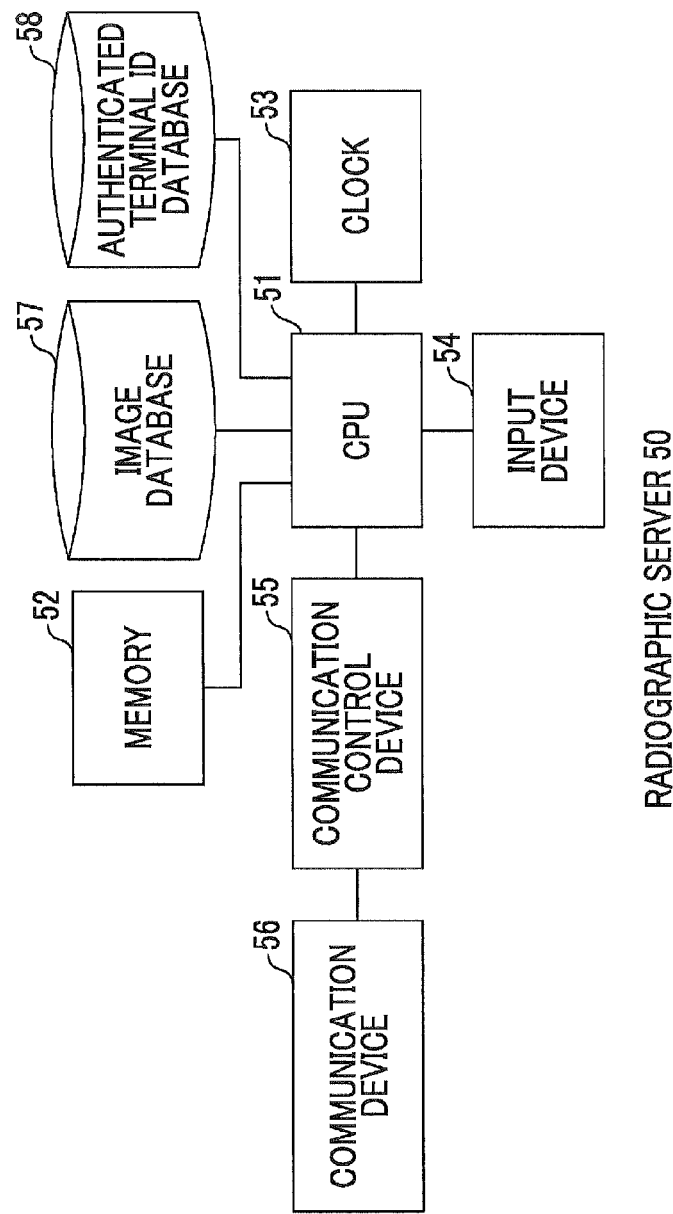
FIG. 6 is a block diagram illustrating the electrical configuration of a radiographic server 50.

FIG. 6 is a block diagram illustrating the electrical configuration of the radiographic server 50.

The overall operation of the radiographic server 50 is controlled by a CPU 51.

The radiographic server 50 includes a memory 52 that stores predetermined data and programs, a clock 53, and an input device 54 such as a keyboard. In addition, the radiographic server 50 includes a communication device 56 that communicates with, for example, the authentication server 40 and a communication control device 55 that controls the communication device 56, as described above. The radiographic server 50 is connected to an image database 57 that stores radiological images and an authenticated terminal ID database 58 that stores the ID of the authenticated portable terminal apparatus 1.

FIG. 7 shows an example of an authenticated terminal ID table stored in the authenticated terminal ID database 58.

The authenticated terminal ID table stores an authenticated terminal ID which is the ID of the authenticated portable terminal apparatus 1. The portable terminal apparatus 1 can control the radiographic apparatus 20 on the basis of the authenticated terminal ID stored in the authenticated terminal ID table.

In addition, the authenticated terminal ID table stores access permission date and time, which is the data and time when the portable terminal apparatus 1 is authenticated, in association with the authenticated terminal ID. In this embodiment, in the case where a predetermined period (second period) has elapsed from the access permission date and time, the CPU 51, which serves as a cancellation unit, deletes the authenticated terminal ID from the authenticated terminal ID table. In this way, it is possible to prevent the portable terminal apparatus 1 which has been authenticated once from limitlessly controlling the radiographic apparatus 20.

Figure 8:
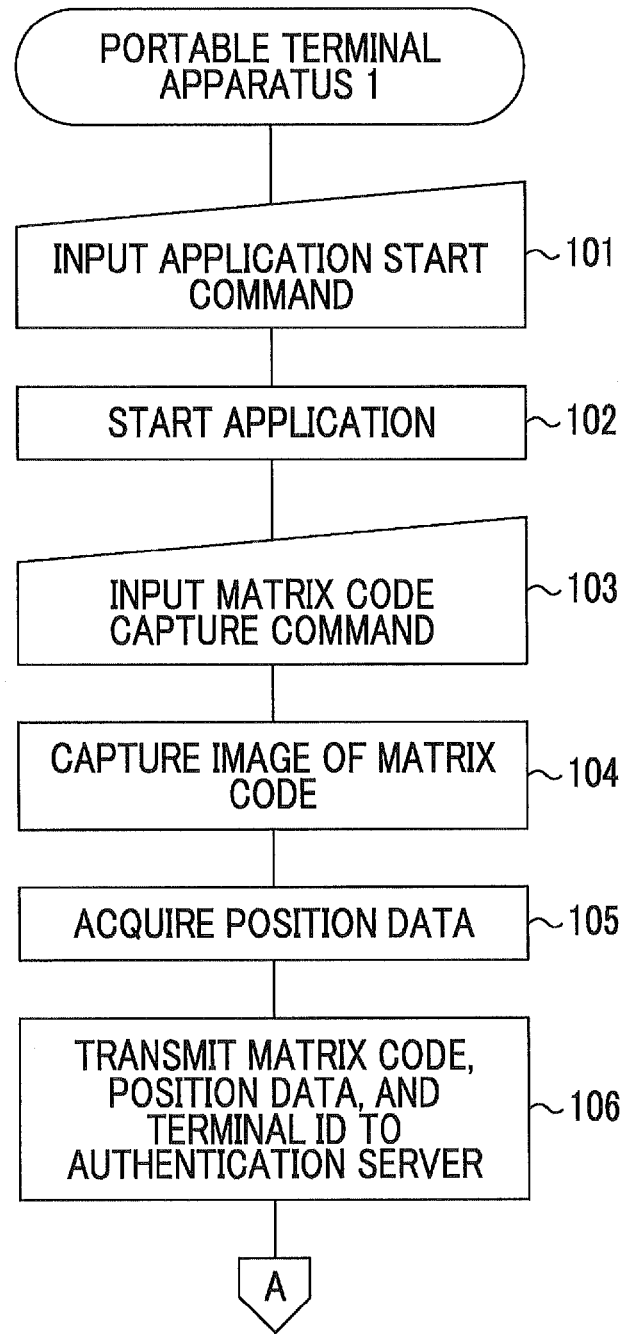
FIG. 8 is a flowchart illustrating the process of a portable terminal apparatus.
Figure 9:
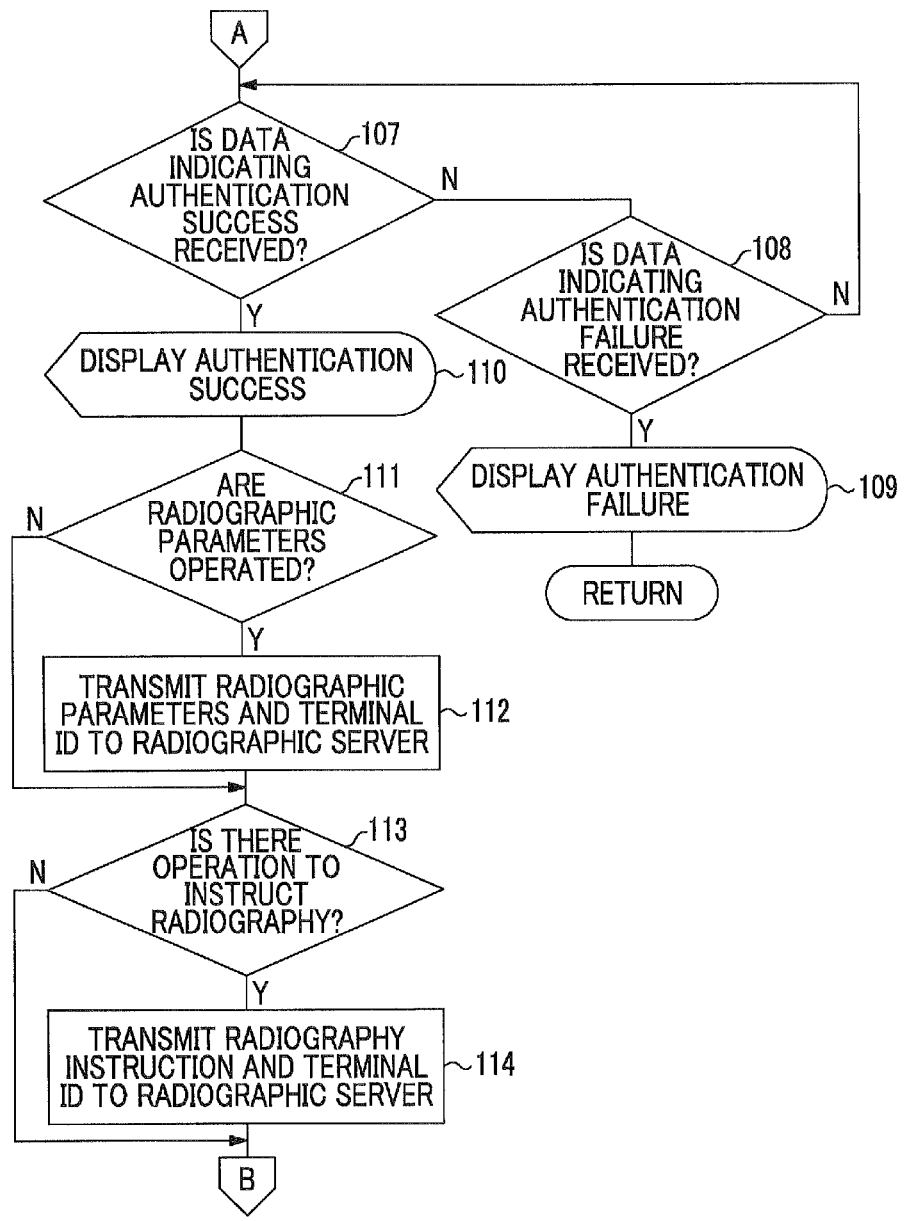
FIG. 9 is a flowchart illustrating the process of the portable terminal apparatus.
Figure 10:
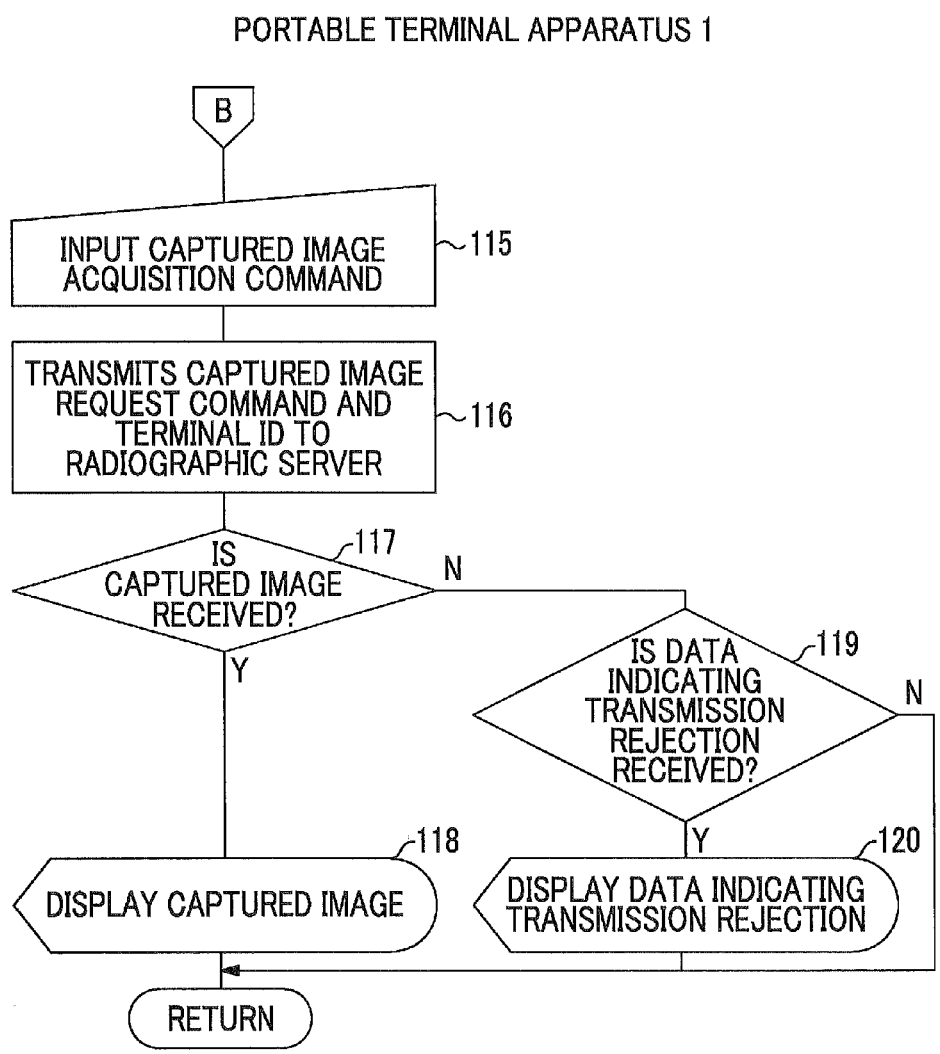
FIG. 10 is a flowchart illustrating the process of the portable terminal apparatus.
Figure 11:
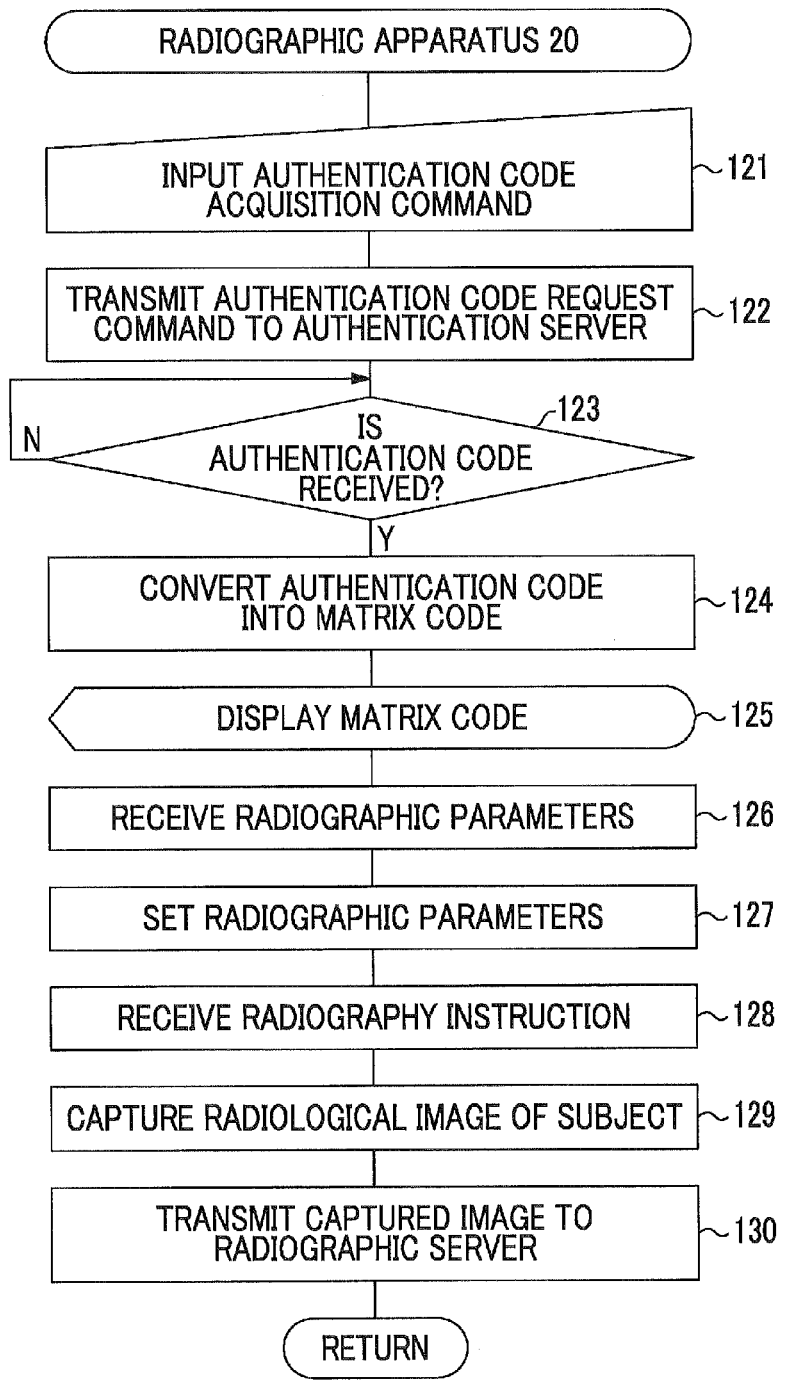
FIG. 11 is a flowchart illustrating the process of the radiographic apparatus.
Figure 12:
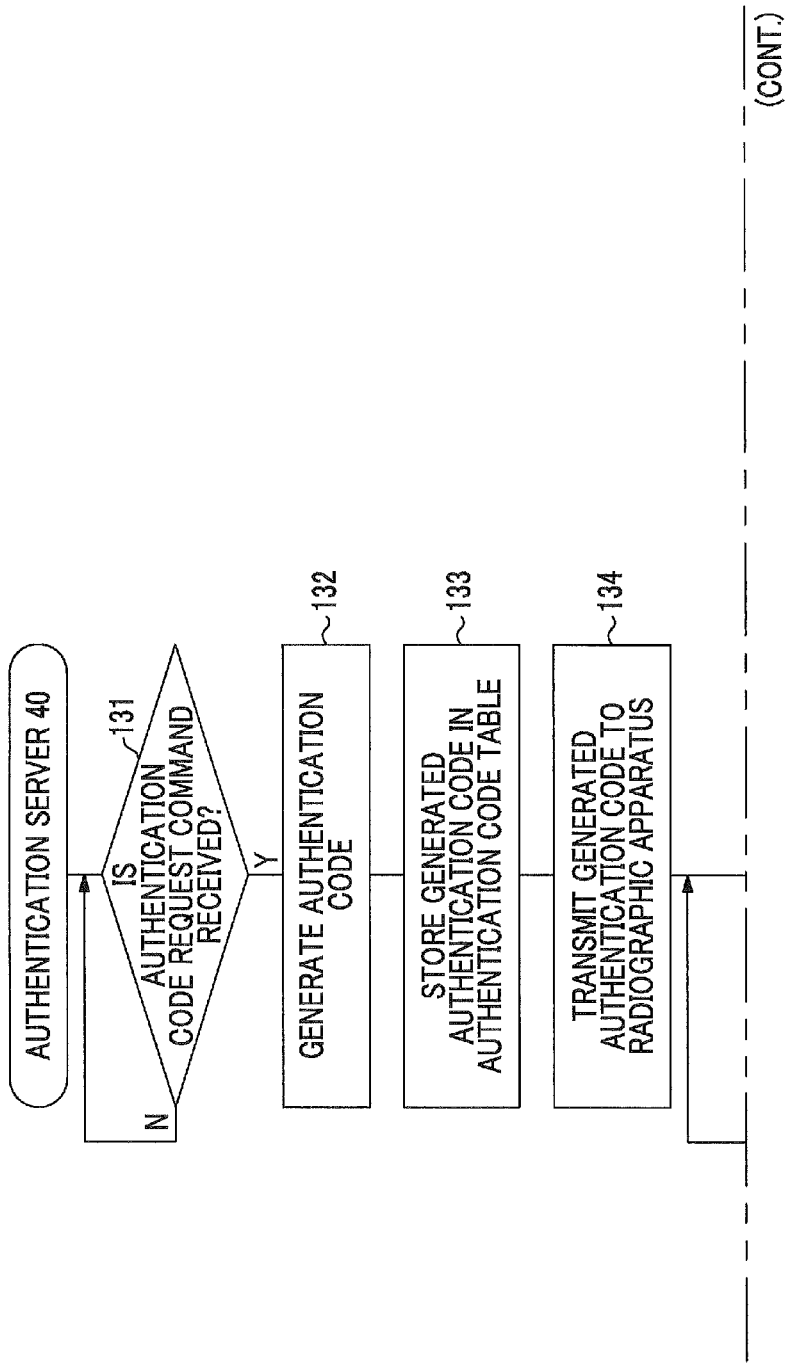
FIG. 12 is a flowchart illustrating the process of the authentication server.
Figure 13:
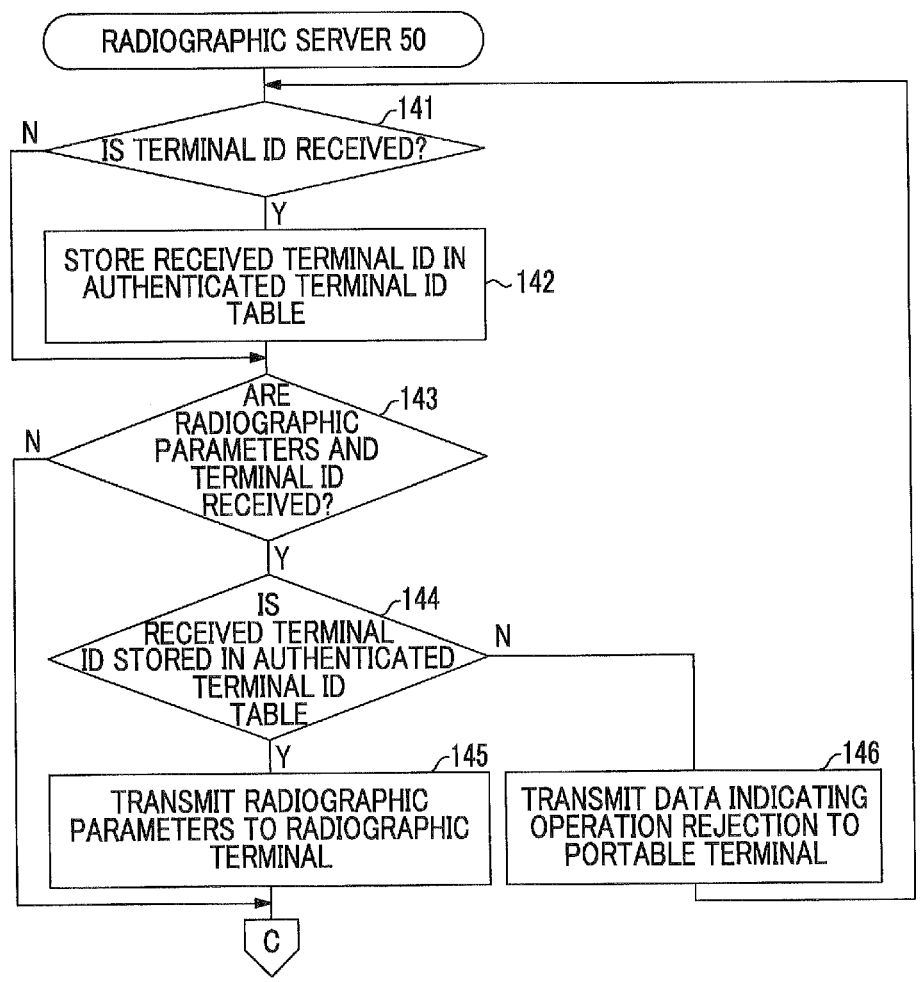
FIG. 13 is a flowchart illustrating the process of a radiographic server.
Figure 14:
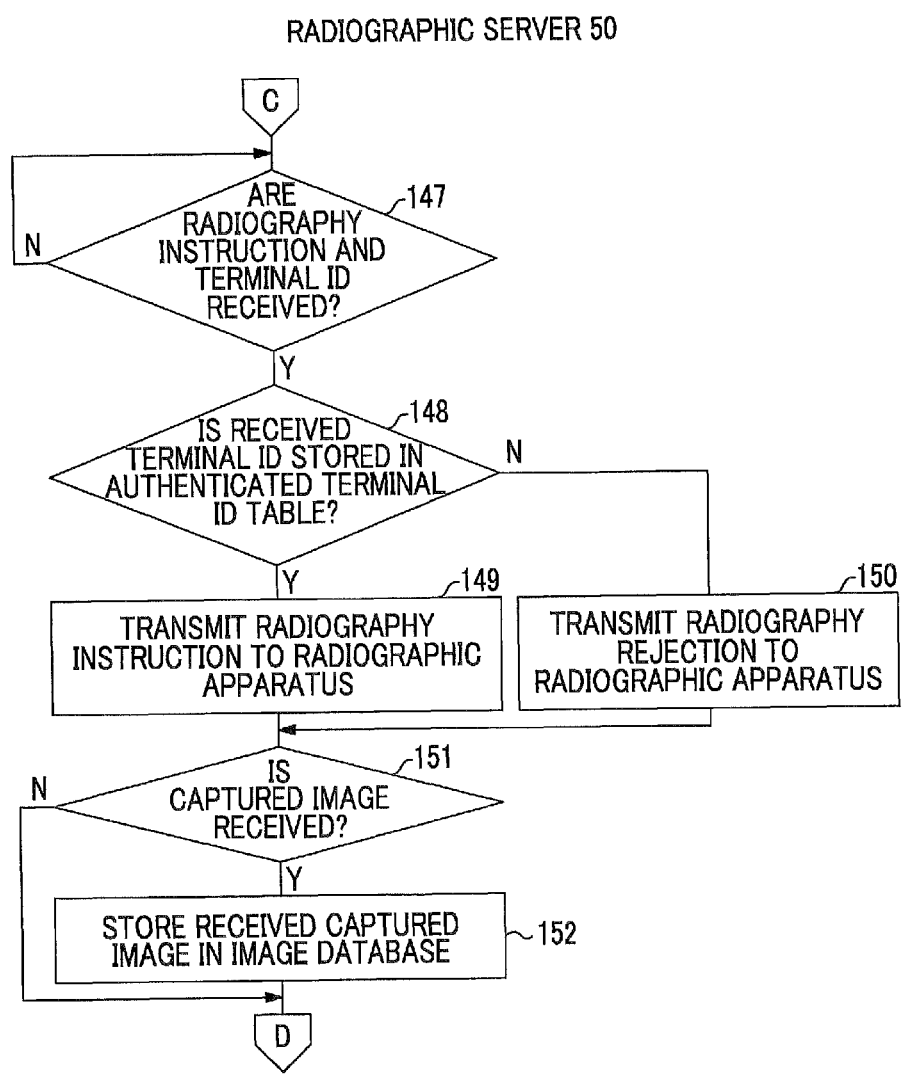
FIG. 14 is a flowchart illustrating the process of the radiographic server.
Figure 15:
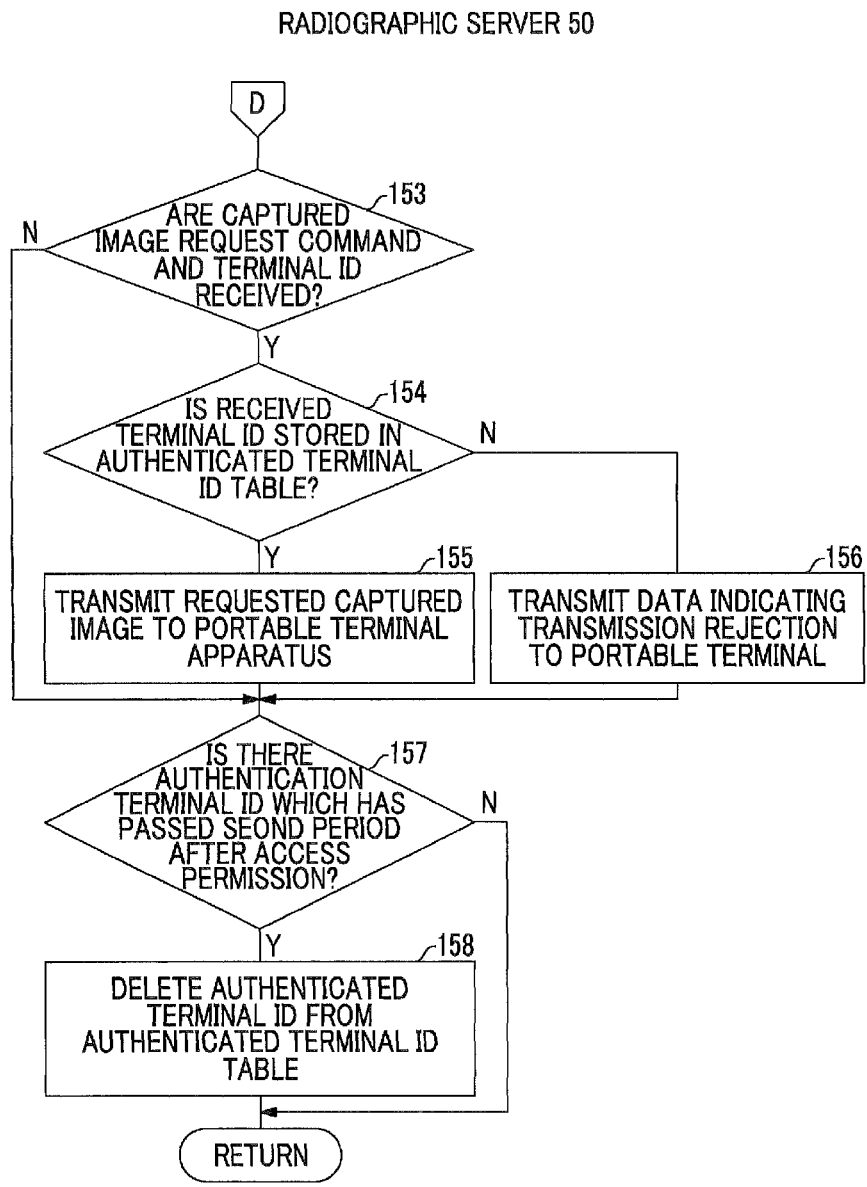
FIG. 15 is a flowchart illustrating the process of the radiographic server.

FIGS. 8 to 10 are flowcharts illustrating the process of the portable terminal apparatus 1. FIG. 11 is a flowchart illustrating the process of the radiographic apparatus 20. FIG. 12 is a flowchart illustrating the process of the authentication server 40. FIGS. 13 to 15 are flowcharts illustrating the process of the radiographic server 50.

In this embodiment, the matrix code indicating the authentication code is displayed on the display device 26 (authentication code output unit) of the radiographic apparatus 20. The operator 100 with the portable terminal apparatus 1 enters the radiographic room 70 and takes an image of the displayed matrix code using the imaging device 9 (code input unit) of the portable terminal apparatus 1. The communication device 11 serving as a code transmitting unit transmits the captured matrix code and position data indicating the position of the portable terminal apparatus 1 to the authentication server 40. In the authentication server 40, in the case where the CPU 41 serving as a determining unit determines that the matrix code transmitted from the portable terminal apparatus 1 is the authentication code, the first period (for example, the time required for a test, such as one hour or one day) has not elapsed from the time when the authentication code has been generated, and the portable terminal apparatus 1 is disposed in the radiographic room 70, it is considered that the operator 100 has authority to operate the radiographic apparatus 20 since the operator 100 is permitted to enter the radiographic room 70. Therefore, the portable terminal apparatus 1 can be used to control the radiographic apparatus 20. The details will become apparent from the following description.

The operator 100 with the portable terminal apparatus 1 enters the radiographic room 70 and inputs a command to start an application for controlling the radiographic apparatus 20 to the portable terminal apparatus 1 (Step 101 of FIG. 8). Then, the application for controlling the radiographic apparatus 20 of the portable terminal apparatus 1 starts (Step 102 of FIG. 8).

First, the operator inputs an authentication code acquisition command to the radiographic apparatus 20 (Step 121 of FIG. 11). Then, the radiographic apparatus 20 transmits an authentication code request command to the authentication server 40 (Step 122 of FIG. 11).

When the authentication server 40 receives the authentication code request command transmitted from the radiographic apparatus 20 (YES in Step 131 of FIG. 12), the CPU 41 (authentication code generating unit) of the authentication server 40 generates an authentication code (Step 132 of FIG. 12). The generated authentication code and the date and time when the authentication code is generated are stored in the authentication code table (see FIG. 5) (Step 133 of FIG. 12). The generated authentication code is transmitted from the communication device 46 (authentication code transmitting unit) of the authentication server 40 to the radiographic apparatus 20 (Step 134 of FIG. 12).

When the radiographic apparatus 20 receives the authentication code transmitted from the authentication server 40 (YES in Step 123 of FIG. 11), the received authentication code is converted into a matrix code (Step 124 of FIG. 11). Then, the converted matrix code is displayed on the display screen of the display device 26 of the radiographic apparatus 20 (Step 125 of FIG. 11).

Confirming that the matrix code is displayed on the display screen of the display device 26 of the radiographic apparatus 20, the operator 100 takes an image of the matrix code using the portable terminal apparatus 1 (Step 104 of FIG. 8). In addition, position data indicating the position of the portable terminal apparatus 1 is acquired by the GPS 6 provided in the portable terminal apparatus 1 (Step 105 of FIG. 8). The captured matrix code, the acquired position data, and the terminal ID of the portable terminal apparatus 1 (a unique terminal ID is stored in the memory 7 of the portable terminal apparatus 1) are transmitted from the communication device 9 of the portable terminal apparatus 1 to the authentication server 40 (Step 106 of FIG. 8). That is, in this embodiment, the communication device 11 corresponds to a code transmitting unit and a position data transmitting unit.

When the authentication server 40 receives the matrix code, the position data, and the terminal ID transmitted from the portable terminal apparatus 1 (YES in Step 135 of FIG. 12), the CPU 41 serving as the determining unit checks whether the first period has elapsed from the generation time of the authentication code indicated by the received matrix code and whether the position indicated by the received position data is the radiographic room 70 (radiographic apparatus 20) (Step 136 of FIG. 12). In the case where the authentication code indicated by the received matrix code is stored in the authentication code table and the first period has not elapsed from the date and time when the authentication code has been generated, it is determined that the authentication code is valid. In addition, data indicating the position of the radiographic room 70 may be stored in the memory 42 of the authentication server 40 in advance.

In the case where the matrix code is valid and the position data indicates the position of the radiographic room 70 (YES in Step 136 of FIG. 12), it is considered that, for example, the matrix code is transmitted from the portable terminal apparatus 1 of the operator 100 in the radiographic room 70. Therefore, the portable terminal apparatus 1 is authenticated. The data indicating that authentication has succeeded is transmitted from the authentication server 40 to the portable terminal apparatus 1 (Step 137 of FIG. 12). In addition, the terminal ID of the portable terminal apparatus 1 is transmitted from the communication device 46 (determination result transmitting unit) of the authentication server 40 to the radiographic server 50 (Step 138 of FIG. 12).

In the case where the matrix code is invalid or the position data does not indicate the position of the radiographic room 70, it is considered that the operator 100 is not disposed in the radiographic room 70 and authentication fails. Data indicating that authentication has failed is transmitted from the authentication server 40 to the portable terminal apparatus 1 (Step 139 of FIG. 12).

In the case where the authentication is successful, the terminal ID is transmitted from the authentication server 40 to the radiographic server 50, and the radiographic server 50 receives the terminal ID (YES in Step 141 of FIG. 13), the received terminal ID is stored in an authenticated terminal ID field of the authenticated terminal ID table (Step 142 of FIG. 13). In addition, the time when the terminal ID is received is stored as the access permission date and time in the authenticated terminal ID table in association with the terminal ID.

In the case where the portable terminal apparatus 1 receives data indicating that authentication has succeeded from the authentication server 40 (YES in Step 107 of FIG. 9), information indicating that authentication has succeeded is displayed on the display screen of the display device 3 of the portable terminal apparatus 1 (Step 110 of FIG. 9). In this way, the operator 100 knows that the radiographic apparatus 20 can be controlled by the portable terminal apparatus 1. In the case where the portable terminal apparatus 1 receives data indicating that authentication has failed from the authentication server 40 (NO in Step 107 and YES in Step 108 of FIG. 9), information indicating that authentication has failed is displayed on the display screen of the display device 3 of the portable terminal apparatus 1 (Step 109 of FIG. 9). The operator 100 may perform the authentication process again, if necessary.

In the case where the authentication of the portable terminal apparatus 1 succeeds, as described above, the operator 100 can control the radiographic apparatus 20 both inside and outside the radiographic room 70 using the portable terminal apparatus 1. When the portable terminal apparatus 1 operates the radiographic parameters of the radiographic apparatus 20 (YES in Step 111 of FIG. 9), the radiographic parameters and the terminal ID of the portable terminal apparatus 1 are transmitted from the portable terminal apparatus 1 to the radiographic server 50 (Step 112 of FIG. 9). The radiographic parameters include, for example, the X-ray dose from the radiographic apparatus 20. The X-ray dose from the radiographic apparatus 20 is controlled by the radiographic parameters.

When the radiographic server 50 receives the radiographic parameters and the terminal ID transmitted from the portable terminal apparatus 1 (YES in Step 143 of FIG. 13), the CPU 51 serving as a permission unit checks whether the received terminal ID is stored in the authenticated terminal ID table (Step 144 of FIG. 13). In the case where the received terminal ID is stored in the authenticated terminal ID table (YES in Step 144 of FIG. 13), the radiographic parameters are transmitted from the radiographic server 50 to the radiographic apparatus 20 since it is confirmed that there is a request to set the radiographic parameters from the authenticated portable terminal apparatus 1 (FIG. 13 Step 145). In the case where the received terminal ID is not stored in the authenticated terminal ID table (NO in Step 144 of FIG. 13), it is determined that the portable terminal apparatus 1 is not authenticated on the basis of the received terminal ID and data indicating operation rejection is transmitted from the radiographic server 50 to the portable terminal apparatus 1 (Step 146 of FIG. 13). In the case where the portable terminal apparatus 1 receives the data indicating the operation rejection, the authentication process is performed if necessary.

When the radiographic apparatus 20 receives the radiographic parameters transmitted from the radiographic server 50 (Step 126 of FIG. 11), the received radiographic parameters are set to the radiographic apparatus 20 (Step 127 of FIG. 11). For example, in the case where the radiographic parameters define the X-ray dose, radiography is performed with the X-ray dose defined by the radiographic parameters.

When the operator 100 operates the portable terminal apparatus 1 to instruct the radiographic apparatus 20 to perform radiography (YES in Step 113 of FIG. 9), the radiography instruction and the terminal ID are transmitted from the portable terminal apparatus 1 to the radiographic server 50 (Step 114 of FIG. 9).

When the radiographic server 50 receives the radiography instruction and the terminal ID transmitted from the portable terminal apparatus 1 (YES in Step 147 of FIG. 14), the CPU 51 serving as the permission unit checks whether the received terminal ID is stored in the authenticated terminal ID table (Step 148 of FIG. 14). In the case where the received terminal ID is stored in the authenticated terminal ID table (YES in Step 148 of FIG. 14), the radiography instruction is transmitted from the radiographic server 50 to the radiographic apparatus 20 (Step 149 of FIG. 14). In the case where the received terminal ID is not stored in the authenticated terminal ID table (NO in Step 148 of FIG. 14), data indicating radiography rejection is transmitted from the radiographic server 50 to the portable terminal apparatus 1 (Step 150 of FIG. 14). When the portable terminal apparatus 1 receives the data indicating a radiography rejection, the authentication process may be performed again.

When the radiographic apparatus 20 receives the radiography instruction transmitted from the radiographic server 50 (Step 128 of FIG. 11), the radiographic apparatus 20 captures the radiological image of the subject in response to the radiography instruction (Step 129 of FIG. 11). The radiological image obtained by radiography is displayed on the display screen of the display device 26 of the radiographic apparatus 20 and is also transmitted from the radiographic apparatus 20 to the radiographic server 50 (Step 130 of FIG. 11).

When the radiographic server 50 receives the captured image transmitted from the radiographic apparatus 20 (YES in Step 151 of FIG. 14), the received captured image is stored in the image database 57 by the radiographic server 50 (Step 152 of FIG. 14).

When the operator 100 inputs a captured image acquisition command to the portable terminal apparatus 1 (Step 113 of FIG. 9), a captured image request command and the terminal ID are transmitted from the portable terminal apparatus 1 to the radiographic server 50 (FIG. 9 Step 114).

When the radiographic server 50 receives the captured image request command and the terminal ID transmitted from the portable terminal apparatus 1 (YES in Step 153 of FIG. 15), the CPU 51 serving as the permission unit checks whether the received terminal ID is stored in the authenticated terminal ID table (Step 154 of FIG. 15). When the received terminal ID is stored in the authenticated terminal ID table (YES in Step 154 of FIG. 15), the requested captured image is read from the image database 57 and the read captured image is transmitted from the radiographic server 50 to the portable terminal apparatus 1 (Step 155 of FIG. 15). When the received terminal ID is not stored in the authenticated terminal ID table (NO in Step 154 of FIG. 15), data indicating transmission rejection is transmitted from the radiographic server 50 to the portable terminal apparatus 1 (Step 156 of FIG. 15).

In the case where the portable terminal apparatus 1 receives the captured image transmitted from the radiographic server 50 (YES in Step 117 of FIG. 10), the received captured image is displayed on the display screen of the display device 3 of the portable terminal apparatus 1 (Step 118 of FIG. 10). In the case where the portable terminal apparatus 1 does not receive the captured image (NO in Step 117 of FIG. 10) and the data indicating transmission rejection is received (YES in Step 119 of FIG. 10), information indicating transmission rejection is displayed on the display screen of the display device 3 of the portable terminal apparatus 1 (Step 120 of FIG. 10).

In the case where there is an authenticated terminal ID which has passed the second period (for example, one hour) from the access permission date and time among the authenticated terminal IDs stored in the authenticated terminal ID table in the authenticated terminal ID database 58 of the radiographic server 50 (YES in Step 157 of FIG. 15), the CPU 51 serving as the cancellation unit deletes such authenticated terminal ID from the authenticated terminal ID table (Step 158 of FIG. 15). In this way, it is possible to prevent the portable terminal apparatus 1 which has been authenticated once from limitlessly controlling the radiographic apparatus 20.

In the above-described embodiment, the authentication server 40 and the radiographic server 50 are provided in addition to the radiographic apparatus 20. However, the radiographic apparatus 20 may perform at least one of the functions of the authentication server 40 and the radiographic server 50. In this case, at least one of the authentication server 40 and the radiographic server 50 may be omitted.

In the above-described embodiment, the authentication server 40 generates the authentication code which is valid for the first period in response to the reception of the authentication code request command form the radiographic apparatus 20 (Step 132 of FIG. 12). However, the authentication server 40 may generate the authentication code which is updated at a predetermined interval and transmit the latest authentication code to the radiographic apparatus 20 in response to the reception of the authentication code request command from the radiographic apparatus 20.

In the above-described embodiment, authentication succeeds in the case where the GPS device 6 of the portable terminal apparatus 1 is used to detect that the portable terminal apparatus 1 is in the radiographic room 70 and the authentication code is correct. However, the authentication process may be performed by checking only the authentication code, without checking the position. In addition, in the above-described embodiment, the radiographic server 50 deletes the terminal ID which has passed the second period from the access permission date and time from the authenticated terminal ID table. However, the authentication server 40, not the radiographic server 50, may perform the deletion process. In this case, the same table as the authenticated terminal ID table may be stored in the authentication server 40 and the authenticated terminal ID which is to be deleted due to the elapse of the second period from the access permission date and time may be transmitted from the authentication server 40 to the radiographic server 50.

In the above-described embodiment, the period for which the authentication code is valid or the interval at which the authentication code is periodically updated, and the period from the access permission date and time to the deletion of the terminal ID from the authenticated terminal ID table may be equal to or different from each other.

In the above-described embodiment, the portable terminal apparatus 1 is used to control the radiographic apparatus 20. However, a controlled apparatus other than the radiographic apparatus 20 may be controlled. In this case, the position of the controlled apparatus may be checked. In the above-described embodiment, the matrix code indicating the authentication code is displayed and used for authentication. However, the authentication code, not the matrix code, may be displayed. Instead of being displayed, the code may be output as a sound as long as it can be recognized by the operator 100. In the case where the code is displayed, the displayed code may be input to the portable terminal apparatus 1 by the operator 100. In the case where the code is output as a sound, the sound which the operator 100 hears may be input to the portable terminal apparatus 1.

What is claimed is:

1. A control system comprising:
a controlled apparatus; and
a portable terminal apparatus that controls the controlled apparatus, the controlled apparatus including:
an authentication code generating unit that generates an authentication code; and
an authentication code output unit that outputs the authentication code generated by the authentication code generating unit,
the portable terminal apparatus including:
a code input unit that inputs a code; and
a code transmitting unit that transmits the code input from the code input unit to the controlled apparatus,
the controlled apparatus further including:
a determining unit that determines whether the code transmitted from the code transmitting unit of the portable terminal apparatus is the authentication code output from the authentication code output unit of the controlled apparatus and whether a first period has elapsed since generation of the authentication code by the authentication code generating unit of the controlled apparatus; and
a permission unit that permits control using the portable terminal apparatus in response to determination by the determining unit that the code transmitted from the code transmitting unit of the portable terminal apparatus is the authentication code output from the authentication code output unit of the controlled apparatus and the first period has not elapsed,
wherein the controlled apparatus is arranged in an authentication area, and
wherein the portable terminal apparatus controls the controlled apparatus both inside and outside the authentication area;
wherein the portable terminal apparatus further includes a position data transmitting unit that transmits data indicating a position of the portable terminal apparatus to the controlled apparatus in response to input of the code from the code input unit,
wherein the determining unit of the controlled apparatus determines whether the code transmitted from the code transmitting unit of the portable terminal apparatus is the authentication code output from the authentication code output unit of the controlled apparatus, whether the first period has elapsed, and whether the position data transmitted from the position data transmitting unit of the portable terminal apparatus indicates a position of the controlled apparatus, and
wherein the permission unit of the controlled apparatus permits the control using the portable terminal apparatus in response to determination by the determining unit that the code transmitted from the code transmitting unit of the portable terminal apparatus is the authentication code output from the authentication code output unit of the controlled apparatus, the first period has not elapsed, and the position data transmitted from the position data transmitting unit of the portable terminal apparatus indicates the position of the controlled apparatus;
wherein, in a case where the code transmitted from the code transmitting unit of the portable terminal apparatus is the authentication code output from the authentication code output unit of the controlled apparatus, information indicating that authentication has succeeded is displayed on a display unit of the portable terminal apparatus.

2. The control system according to claim 1,
wherein the controlled apparatus further includes a cancellation unit that cancels permission of the control using the portable terminal apparatus in response to elapse of a second period since the permission by the permission unit.

3. The control system according to claim 2,
wherein the portable terminal apparatus further includes a position data transmitting unit that transmits data indicating a position of the portable terminal apparatus to the controlled apparatus in response to input of the code from the code input unit,
wherein the determining unit of the controlled apparatus determines whether the code transmitted from the code transmitting unit of the portable terminal apparatus is the authentication code output from the authentication code output unit of the controlled apparatus, whether the first period has elapsed, and whether the position data transmitted from the position data transmitting unit of the portable terminal apparatus indicates a position of the controlled apparatus, and
wherein the permission unit of the controlled apparatus permits the control using the portable terminal apparatus in response to determination by the determining unit that the code transmitted from the code transmitting unit of the portable terminal apparatus is the authentication code output from the authentication code output unit of the controlled apparatus, the first period has not elapsed, and the position data transmitted from the position data transmitting unit of the portable terminal apparatus indicates the position of the controlled apparatus.

4. The control system according to claim 1, wherein the controlled apparatus further comprises: a controlled apparatus body; an authentication server; and a control server, which are configured to communicate with one another, wherein the authentication server includes:
the authentication code generating unit; and
an authentication code transmitting unit that transmits the authentication code generated by the authentication code generating unit to the controlled apparatus body, wherein the controlled apparatus body includes the authentication code output unit, the authentication code output unit outputting the authentication code transmitted from the authentication code transmitting unit of the authentication server, wherein the authentication server further includes:
the determining unit; and
a determination result transmitting unit that transmits data indicating a result of the determination by the determining unit to the control server, and wherein the control server includes the permission unit, the permission unit permitting the control based upon the data indicating the result of determination which is transmitted from the determination result transmitting unit of the authentication server.

5. The control system according to claim 2, wherein the controlled apparatus further comprises:
a controlled apparatus body;
an authentication server; and
a control server, which are configured to communicate with one another, wherein the authentication server includes:
the authentication code generating unit; and
an authentication code transmitting unit that transmits the authentication code generated by the authentication code generating unit to the controlled apparatus body, wherein the controlled apparatus body includes the authentication code output unit, the authentication code output unit outputting the authentication code transmitted from the authentication code transmitting unit of the authentication server, wherein the authentication server further includes:
the determining unit; and
a determination result transmitting unit that transmits data indicating a result of the determination by the determining unit to the control server, and wherein the control server includes the permission unit, the permission unit permitting the control based upon the data indicating the result of determination which is transmitted from the determination result transmitting unit of the authentication server.

6. The control system according to claim 1, wherein the controlled apparatus further comprises:
a controlled apparatus body;
an authentication server; and
a control server, which are configured to communicate with one another, wherein the authentication server further includes:
the authentication code generating unit; and
an authentication code transmitting unit that transmits the authentication code generated by the authentication code generating unit to the controlled apparatus body, wherein the controlled apparatus body includes the authentication code output unit, the authentication code output unit outputting the authentication code transmitted from the authentication code transmitting unit of the authentication server, wherein the authentication server further includes:
the determining unit; and
a determination result transmitting unit that transmits data indicating a result of the determination by the determining unit to the control server, and wherein the control server includes the permission unit, the permission unit permitting the control based upon the data indicating the result of determination which is transmitted from the determination result transmitting unit of the authentication server.

7. The control system according to claim 3, wherein the controlled apparatus further comprises:
a controlled apparatus body;
an authentication server; and
a control server, which are configured to communicate with one another, wherein the authentication server further includes:
the authentication code generating unit; and
an authentication code transmitting unit that transmits the authentication code generated by the authentication code generating unit to the controlled apparatus body, wherein the controlled apparatus body includes the authentication code output unit, the authentication code output unit outputting the authentication code transmitted from the authentication code transmitting unit of the authentication server, wherein the authentication server further includes:
the determining unit; and
a determination result transmitting unit that transmits data indicating a result of the determination by the determining unit to the control server, and wherein the control server includes the permission unit, the permission unit permitting the control based upon the data indicating the result of determination which is transmitted from the determination result transmitting unit of the authentication server.

8. The control system according to claim 3,
wherein the controlled apparatus is arranged in an authentication area, and
wherein the portable terminal apparatus controls the controlled apparatus both inside and outside the authentication area.

9. The control system according to claim 4,
wherein the controlled apparatus is arranged in an authentication area, and
wherein the portable terminal apparatus controls the controlled apparatus both inside and outside the authentication area.

10. A controlled apparatus that is controlled by a portable terminal apparatus, comprising:
an authentication code generating unit that generates an authentication code;
an authentication code output unit that outputs the authentication code generated by the authentication code generating unit;
a determining unit that determines whether a code transmitted from the portable terminal apparatus is the authentication code output from the authentication code output unit and whether a first period has elapsed since generation of the authentication code by the authentication code generating unit; and
a permission unit that permits control using the portable terminal apparatus in response to determination by the determining unit that the code transmitted from the portable terminal apparatus is the authentication code output from the authentication code output unit and the first period has not elapsed, wherein the controlled apparatus is arranged in an authentication area, and wherein the portable terminal apparatus controls the controlled apparatus both inside and outside the authentication area;

wherein the portable terminal apparatus further includes a position data transmitting unit that transmits data indicating a position of the portable terminal apparatus to the controlled apparatus in response to input of the code from the code input unit, wherein the determining unit of the controlled apparatus determines whether the code transmitted from the code transmitting unit of the portable terminal apparatus is the authentication code output from the authentication code output unit of the controlled apparatus, whether the first period has elapsed, and whether the position data transmitted from the position data transmitting unit of the portable terminal apparatus indicates a position of the controlled apparatus, and wherein the permission unit of the controlled apparatus permits the control using the portable terminal apparatus in response to determination by the determining unit that the code transmitted from the code transmitting unit of the portable terminal apparatus is the authentication code output from the authentication code output unit of the controlled apparatus, the first period has not elapsed, and the position data transmitted from the position data transmitting unit of the portable terminal apparatus indicates the position of the controlled apparatus;

wherein, in a case where the code transmitted from the code transmitting unit of the portable terminal apparatus is the authentication code output from the authentication code output unit of the controlled apparatus, information indicating that authentication has succeeded is displayed on a display unit of the portable terminal apparatus.

11. A method of controlling an operation of a control system including a controlled apparatus and a portable terminal apparatus that controls the controlled apparatus, comprising:

generating an authentication code using an authentication code generating unit of the controlled apparatus;

outputting the authentication code generated by the authentication code generating unit using an authentication code output unit of the controlled apparatus;

inputting a code using a code input unit of the portable terminal apparatus;

transmitting the code input from the code input unit to the controlled apparatus using a code transmitting unit of the portable terminal apparatus;

determining whether the code transmitted from the code transmitting unit of the portable terminal apparatus is the authentication code output from the authentication code output unit of the controlled apparatus and whether a first period has elapsed from a time since generation of the authentication code by the authentication code generating unit of the controlled apparatus using a determining unit of the controlled apparatus; and permitting control using the portable terminal apparatus in response to determination by the determining unit that the code transmitted from the code transmitting unit of the portable terminal apparatus is the authentication code output from the authentication code output unit of the controlled apparatus and the first period has not elapsed using a permission unit of the controlled apparatus, wherein the controlled apparatus is arranged in an authentication area, and wherein the portable terminal apparatus controls the controlled apparatus both inside and outside the authentication area;

wherein the portable terminal apparatus further includes a position data transmitting unit that transmits data indicating a position of the portable terminal apparatus to the controlled apparatus in response to input of the code from the code input unit, wherein the determining unit of the controlled apparatus determines whether the code transmitted from the code transmitting unit of the portable terminal apparatus is the authentication code output from the authentication code output unit of the controlled apparatus, whether the first period has elapsed, and whether the position data transmitted from the position data transmitting unit of the portable terminal apparatus indicates a position of the controlled apparatus, and wherein the permission unit of the controlled apparatus permits the control using the portable terminal apparatus in response to determination by the determining unit that the code transmitted from the code transmitting unit of the portable terminal apparatus is the authentication code output from the authentication code output unit of the controlled apparatus, the first period has not elapsed, and the position data transmitted from the position data transmitting unit of the portable terminal apparatus indicates the position of the controlled apparatus;

wherein, in a case where the code transmitted from the code transmitting unit of the portable terminal apparatus is the authentication code output from the authentication code output unit of the controlled apparatus, information indicating that authentication has succeeded is displayed on a display unit of the portable terminal apparatus.

12. A method of controlling an operation of a controlled apparatus that is controlled by a portable terminal apparatus, comprising:

generating an authentication code using an authentication code generating unit;

outputting the authentication code generated by the authentication code generating unit using an authentication code output unit;

determining whether a code transmitted from the portable terminal apparatus is the authentication code output from the authentication code output unit of the controlled apparatus and whether a first period has elapsed from a time when the authentication code has been generated by the authentication code generating unit of the controlled apparatus using a determining unit; and permitting control using the portable terminal apparatus in response to determination by the determining unit that the code transmitted from the portable terminal apparatus is the authentication code output from the authentication code output unit of the controlled apparatus and the first period has not elapsed using a permission unit, wherein the controlled apparatus is arranged in an authentication area, and wherein the portable terminal apparatus controls the controlled apparatus both inside and outside the authentication area;

wherein the portable terminal apparatus further includes a position data transmitting unit that transmits data indicating a position of the portable terminal apparatus to the controlled apparatus in response to input of the code from the code input unit, wherein the determining unit of the controlled apparatus determines whether the code transmitted from the code transmitting unit of the portable terminal apparatus is the authentication code output from the authentication code output unit of the controlled apparatus, whether the first period has elapsed, and whether the position data transmitted from the position data transmitting unit of the portable terminal apparatus indicates a position of the controlled apparatus, and wherein the permission unit of the controlled apparatus permits the control using the portable terminal apparatus in response to determination by the determining unit that the code transmitted from the code transmitting unit of the portable terminal apparatus is the authentication code output from the authentication code output unit of the controlled apparatus, the first period has not elapsed, and the position data transmitted from the position data transmitting unit of the portable terminal apparatus indicates the position of the controlled apparatus;

wherein, in a case where the code transmitted from the code transmitting unit of the portable terminal apparatus is the authentication code output from the authentication code output unit of the controlled apparatus, information indicating that authentication has succeeded is displayed on a display unit of the portable terminal apparatus.

13. The method according to claim 11, further comprising canceling permitting of the control using the portable terminal apparatus in response to elapse of a second period since the permitting by the permission unit.

14. The method according to claim 12, further comprising canceling permitting of the control using the portable terminal apparatus in response to elapse of a second period since the permitting by the permission unit.

15. The control system according to claim 1, wherein the portable terminal apparatus further includes a display unit,
wherein, in a case where the code transmitted from the code transmitting unit of the portable terminal apparatus is not the authentication code output from the authentication code output unit of the controlled apparatus, information indicating that authentication has failed is displayed on the display unit of the portable terminal apparatus.

16. The control system according to claim 1, wherein the authentication code comprises at least one of:
a matrix code;
a bar-code;
numbers; and/or
characters.

17. The control system according to claim 1, wherein the authentication code generated by the authentication code generating unit is updated at a predetermined interval,
wherein the authentication code output unit outputs a latest authentication code to the controlled apparatus.

* * * * *